(12) United States Patent
Pirotte et al.

(10) Patent No.: US 6,894,043 B1
(45) Date of Patent: May 17, 2005

(54) BENZOTHIADIAZINE DERIVATIVES, PREPARATION METHOD AND PHARMACEUTICAL COMPOSITIONS CONTAINING SAME

(75) Inventors: Bernard Pirotte, Oupeye (BE); Pascal De Tullio, Jupille sur Liege (BE); Stéphane Boverie, Bierset (BE); Isabelle Kempen, Pepinster (BE); Pierre Lestage, La Celle St Cloud (FR)

(73) Assignee: Les Laboratoires Servier, Courbevoie (FR)

( * ) Notice: Subject to any disclaimer, the term of this patent is extended or adjusted under 35 U.S.C. 154(b) by 318 days.

(21) Appl. No.: 10/148,257
(22) PCT Filed: Nov. 28, 2000
(86) PCT No.: PCT/FR00/03313
§ 371 (c)(1),
(2), (4) Date: May 30, 2002
(87) PCT Pub. No.: WO01/40210
PCT Pub. Date: Jun. 7, 2001

(30) Foreign Application Priority Data

Nov. 30, 1999 (FR) .............................................. 99 15034

(51) Int. Cl.$^7$ ................... C07D 285/24; A61K 31/5415
(52) U.S. Cl. ...................................... 514/223.2; 544/11
(58) Field of Search .................. 514/223.2; 544/11, 544/12

(56) References Cited

FOREIGN PATENT DOCUMENTS

| WO | WO 93/21170 | 10/1993 |
|----|-------------|---------|
| WO | WO 93/21171 | 10/1993 |
| WO | WO 95/07899 A | 3/1995 |
| WO | WO 95/07899 | 3/1995 |
| WO | WO 98/12185 | 3/1998 |

OTHER PUBLICATIONS

Chemical Abstracts, vol. 77, No. 25, Abstract No. 164185.

*Primary Examiner*—John M. Ford
(74) *Attorney, Agent, or Firm*—The Firm of Hueschen and Sage

(57) ABSTRACT

Compound selected from those of formula (I):

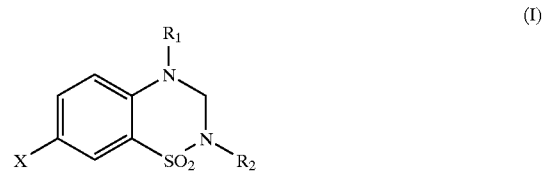

wherein:
X represents flourine, bromine, iodine or methyl,
each of $R_1$ and $R_2$, which may be identical or different, represents hydrogen or alkyl, its isomers when they exist, and addition salts thereof with a pharmaceutically acceptable acid Medicinal products containing the same which are useful as AMPA modulators.

3 Claims, No Drawings

BENZOTHIADIAZINE DERIVATIVES, PREPARATION METHOD AND PHARMACEUTICAL COMPOSITIONS CONTAINING SAME

BACKGROUND OF THE INVENTION

Substances that activate AMPA receptors, by facilitating glutamatergic synaptic transmission in the brain, have therapeutic potential in the treatment of schizophrenia (Patent Specification WO 97/07799) and cognitive disorders associated with cerebral ageing, for example in Alzheimer's disease (Ito et al., J. Physiol. 1990, 424, 543–553).

A certain number of substances (aniracetam, cyclothiazide, diazoxide) are nowadays used for their AMPA receptor-activating properties.

DESCRIPTION OF THE PRIOR ART

Benzothiadiazine compounds are also described as positive allosteric AMPA receptor modulators (Patent Specification WO 98/12185).

It was therefore of particular interest to synthesise new AMPA receptor modulator compounds in order to increase the potency, selectivity and bioavailability of the compounds already described in the literature.

DETAILED DESCRIPTION OF THE INVENTION

More especially, the present invention relates to compounds of formula (I):

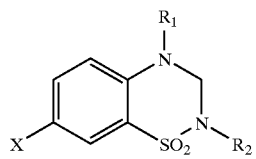

(I)

wherein:
- X represents a fluorine, bromine or iodine atom or a methyl group,
- each of $R_1$ and $R_2$, which may be identical or different, represents a hydrogen atom or a linear or branched $(C_1-C_6)$alkyl group, their isomers when they exist, and addition salts thereof with a pharmaceutically acceptable acid.

Among the pharmaceutically acceptable acids, there may be mentioned by way of non-limiting example hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid.

The invention relates also to a process for the preparation of compounds of formula (I), characterised in that a compound of formula (II):

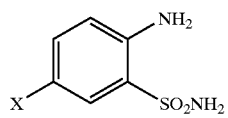

(II)

wherein X is as defined for formula (I), is reacted with ethyl orthoformate,
to yield a compound of formula (III):

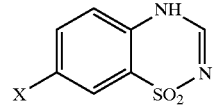

(III)

wherein X is as defined hereinbefore,
which is reacted:
either with a reducing agent, to yield a compound of formula (Ia), a particular case of the compounds of formula (I):

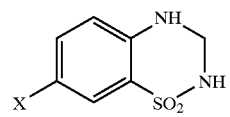

(Ia)

wherein X is as defined hereinbefore,
which is reacted, if desired, with di(tert-butyl) dicarbonate, to yield a compound of formula (IV):

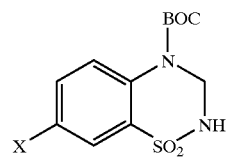

(IV)

wherein X is as defined hereinbefore and BOC represents the group tert-butoxycarbonyl,
which is then reacted with a compound of formula (V):

(V)

wherein $R'_2$ represents a linear or branched $(C_1-C_6)$alkyl group, and $Y_2$ represents a leaving group, such as a halogen atom or a tosylate, mesylate or trifluoromethanesulphonate group,
to yield, after deprotection, a compound of formula (Ib), a particular case of the compounds of formula (I):

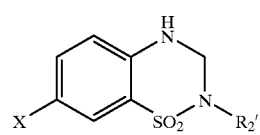

(Ib)

wherein X and $R'_2$ are as defined hereinbefore,
or with a compound of formula (VI):

(VI)

wherein $R'_1$ represents a linear or branched $(C_1-C_6)$alkyl group, and $Y_1$ represents a leaving group, such as a halogen atom or a tosylate, mesylate or trifluoromethanesulphonate group,
to yield, after reduction, a compound of formula (Ic), a particular case of the compounds of formula (I):

wherein X and R'₁ are as defined hereinbefore,
which is reacted, if desired, with a compound of formula (V) to yield a compound of formula (Id), a particular case of the compounds of formula (I):

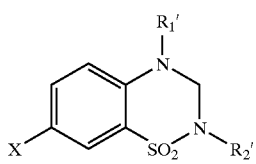

wherein X, R'₁ and R'₂ are as defined hereinbefore,
which compounds of formulae (Ia), (Ib), (Ic) and (Id) constitute the totality of the compounds of formula (I), which are purified, if necessary, according to a conventional purification technique, and converted, if desired, into addition salts thereof with a pharmaceutically acceptable acid.

The compound of formula (II) is obtained according to the process described by Girard et al. (J. Chem. Soc. Perkin 11979, 1043–1047).

In addition to being new, the compounds of the present invention have AMPA receptor-activating properties which make them useful in the treatment of cognitive defects associated with cerebral ageing and neurodegenerative pathologies, such as Alzheimer's disease, Parkinson's disease, Pick's disease, Korsakoff's disease, frontal and sub-cortical dementia, and in the treatment of schizophrenia.

The invention relates also to pharmaceutical compositions comprising as active ingredient at least one compound of formula (I) with one or more suitable, inert, non-toxic excipients. Among the pharmaceutical compositions according to the invention, special mention may be made of those that are suitable for oral, parenteral (intravenous or subcutaneous) or nasal administration, tablets or dragées, sublingual tablets, gelatin capsules, lozenges, suppositories, creams, ointments, dermal gels, injectable preparations, drinkable suspensions, etc.

The useful dosage can be adapted according to the nature and severity of the disorder, the route of adminstration and the age and weight of the patient. The dosage varies from 1 to 500 mg per day in one or more administrations.

The following Examples illustrate the invention but do not limit it in any way.

The starting materials used are known products or are prepared according to known preparation procedures.

The structures of the compounds described in the Examples were determined according to the usual spectrophotometric techniques (infrared, NMR, mass spectrometry).

EXAMPLE 1

7-Fluoro-2,3-dihydro-4H-1,2,4-benzothiadiazine 1,1-dioxide

Step A: 2-Amino-5-fluorobenzenesulphonamide

The expected product is obtained according to the process described in J. Chem. Soc. Perkin I 1979, 1043–1047 starting from 4-fluoroaniline.

Step B: 7-Fluoro-4H-1,2,4-benzothiadiazine 1,1-dioxide 15 ml of ethyl orthoformate are added to 10 mmol of the compound obtained in the preceding Step, and then the mixture is refluxed for 2 hours. After returning to room temperature, the resulting precipitate is filtered off, and then washed and dried to yield the expected product.
Melting point: 260–263° C.
IR (KBr): 3297, 3080, 1607, 1589, 1524, 1492, 1376, 1296, 1219, 1152 and 1134 cm⁻¹

Step C: 7-Fluoro-2,3-dihydro-4H-1,2,4-benzothiadiazine 1,1-dioxide

To 10 mmol of the compound obtained in the preceding Step suspended in water there are added dropwise 10 mmol of 5% aqueous sodium hydroxide m/v, followed by 50 mmol of sodium borohydride in a 5% aqueous solution m/v. After stirring for 1 hour, the pH of the solution is adjusted to 6–7 by adding a 2N hydrochloric acid solution. The resulting precipitate is filtered off, washed and then dried and recrystallised to yield the expected product.
Melting Point: 159–165° C.
IR (KBr): 3372, 3292, 1623, 1504, 1396, 1365, 1316, 1253, 1196 and 1158 cm⁻¹

EXAMPLE 2

7-Bromo-2,3-dihydro-4H-1,2,4-benzothiadiazine 1,1-dioxide

Step A: 7-Bromo-4H-1,2,4-benzothiadiazine 1,1-dioxide

The expected product is obtained according to the process described in Step B of Example 1 starting from 2-amino-5-bromobenzenesulphonamide (described in Il Farmaco 1974, 29 47–57).
Melting point: 279–281° C.
IR (KBr): 3233, 3163, 3082, 3026, 1615, 1577, 1523, 1478, 1376, 1288, 1161, 1142 and 1090 cm⁻¹

Step B: 7-Bromo-2,3-dihydro-4H-1,2,4-benzothiadiazine 1,1-dioxide

The expected product is obtained according to the process described in Step C of Example 1 starting from the compound obtained in the preceding Step.
Melting point: 207–212° C.
IR (KBr): 3421, 3282, 1596, 1498, 1386, 1360, 1319, 1310 and 1155 cm⁻¹

EXAMPLE 3

7-Bromo-4-ethyl-2,3-dihydro-4H-1,2,4-benzothiadiazine 1,1-dioxide

Step A: 7-Bromo-4-ethyl-4H-1,2,4-benzothiadiazine 1,1-dioxide 30 mmol of ethyl bromide and 30 mmol of anhydrous potassium carbonate are added to 10 mmol of the compound obtained in Step A of Example 2 suspended in acetonitrile, and then the mixture is refluxed for 2 hours. The solvent is then evaporated and the resulting solid residue is dispersed in water. The pH of the suspension is immediately adjusted to 7 with a 2N hydrochloric acid solution. The insoluble matter is filtered off, washed and then dried to yield the expected product.
Melting point: 269–273° C.
IR (KBr): 1611, 1584, 1549, 1473, 1434, 1410, 1395, 1305, 1279, 1258, 1162, 1120 and 1102 cm⁻¹

Step B: 7-Bromo-4-ethyl-2,3-dihydro-4H-1,2,4-benzothiadiazine 1,1-dioxide 30 mmol of finely dispersed sodium borohyride are added, in small fractions, to 10 mmol of the compound obtained in the preceding Step suspended in isopropanol.

After 40 minutes' stirring at room temperature, the solvent is removed by evaporation and the resulting solid residue is dispersed in water. The pH of the suspension is then adjusted to 7, and the solid is subsequently filtered off, washed, dried and then recrystallised to yield the expected product.
Melting point: 122–124° C.
IR (KBr): 3222, 2975, 2964, 1594, 1547, 1497, 1470, 1336, 1320, 1263, 1167, 1153 and 1076 cm$^{-1}$

EXAMPLE 4

4-Ethyl-7-iodo-2,3-dihydro-4H-1,2,4-benzothiadiazine 1,1-dioxide

The expected product is obtained according to the process described in Example 3 starting from 7-iodo-4H-1,2,4-benzothiadiazine 1,1-dioxide (described in Il Farmaco 1974, 29, 47–57).
Melting point: 127–128° C.
IR (KBr): 3224, 2972.1588, 1495, 1335, 1319, 1268, 1186, 1153 and 1070 cm$^{-1}$

EXAMPLE 5

4-Ethyl-7-iodo-2-methyl-2,3-dihydro-4H-1,2,4-benzothiadiazine 1,1-dioxide

The expected product is obtained according to the process described in Step A of Example 3 starting from the compound described in Example 4 and methyl iodide.
Melting point: 139–141° C.
IR (KBr): 2972, 1589, 1492, 1458, 1412, 1327, 1261, 1203, 1165, 1154 and 1104 cm$^{-1}$

EXAMPLE 6

4,7-Dimethyl-2,3-dihydro-4H-1,2,4-benzothiadiazine 1,1-dioxide

Step A: 7-Methyl-4H-1,2,4-benzothiadiazine-1,1-dioxide

The expected product is obtained according to the process described in Step B of Example 1 starting from 2-amino-5-methylbenzenesulphonamide (described in J. Chem. Soc. Perkin I 1979, 1043–1047).
Melting point: 298–299° C.
IR (KBr): 3272, 3105, 3042, 1605, 1590, 1522, 1498, 1379, 1286, 1155, 1140 and 1067 cm$^{-1}$ Step B: 4,7-Dimethyl-2,3-dihydro-4H-1,2,4-benzothiadiazine 1,1-dioxide The expected product is obtained according to the process described in Example 3 starting from the compound described in the preceding Step and methyl iodide.
Melting point: 149–151° C.
IR (KBr): 3228, 1619, 1515, 1318, 1297, 1205, 1163, 1148 and 1071 cm$^{-1}$

EXAMPLE 7

4-Ethyl-7-methyl-2,3-dihydro-4H-1,2,4-benzothiadiazine 1,1-dioxide

The expected product is obtained according to the process described in Example 3 starting from the compound described in Step A of Example 6 and ethyl bromide.
Melting point: 110–111° C.
IR (KBr): 3235, 2974, 1621, 1512, 1338, 1316, 1299, 1266, 1251, 1188 and 1152 cm$^{-1}$

EXAMPLE 8

Study of Excitatory Fluxes Induced by AMPA in Xenopus Oocytes mRNAs are prepared from cerebral cortex of male Wistar rat by the guanidium thiocyanate/phenol/chloroform method. The poly(A$^+$)mRNAs are isolated by chromatography on oligo-dT cellulose and injected with 50 ng per oocyte. The oocytes are left for 2 to 3 days' incubation at 10° C. to enable expression of the receptors and are then stored at 8–10° C.

Electrophysiological recording is carried out in a plexiglass chamber at 20–24° C. in an OR2 medium (J. Exp. Zool., 1973, 184, 321–334) by the 2-electrode "voltage-clamp" method, with a 3rd electrode being placed in the bath to serve as reference.

All the compounds are administered via the incubation medium and the electric current is measured at the end of the period of administration. AMPA is used in a concentration of 30 $\mu$M. For each compound studied, there is determined the concentration that doubles (EC2X) or quintuples (EC5X) the intensity of the flux induced by AMPA alone (50 to 100 nA).

The compounds of the invention potentiate the excitatory effects of AMPA considerably. By way of example, the compounds of Examples 3 and 4 have the EC2X and EC5X values given in the Table below.

| Compound | EC2X ($\mu$M) | EC5X ($\mu$M) |
|---|---|---|
| Example 3 | 29 ± 6 | 78 ± 16 |
| Example 4 | 95 ± 31 | >300 |

EXAMPLE 9

Social Recognition in the Wistar Rat

Initially described in 1982 by THOR and HOLLOWAY (J. Comp. Physiol., 1982, 96, 1000–1006), the social recognition test has subsequently been proposed by various authors (DANTZER et al., Psychopharmacology, 1987, 91, 363–368; PERIO et al., Psychopharmacology, 1989, 97, 262–268) for studying the mnemocognitive effects of new compounds. The test is based on the natural expression of the olfactory memory of the rat and its natural tendency to forget and allows evaluation of memorisation, by recognition of a young congeneric animal, by an adult rat. A young rat (21 days), taken at random, is placed for 5 minutes in the cage housing an adult rat. With the aid of a video device, the experimenter observes the social recognition behaviour of the adult rat and measures its overall duration. The young rat is then removed from the adult rat's cage and is placed in its own cage until the second introduction. The adult rat is given the test compound and, after 2 hours, is again brought into the presence (5 minutes) of the young rat. The social recognition behaviour is then observed again and its duration measured. The assessment criterion is the difference ($T_2$-$T_1$), expressed in seconds, between the "recognition" times of the 2 encounters.

The results obtained show a difference ($T_2$-$T_1$) ranging from (−15) to (−30) s for doses ranging from 0.3 to 3 mg/kg, which shows that the compounds of the invention very greatly enhance memorisation, even at a low dose.

EXAMPLE 10

Object Recognition in the Wistar rat

The object recognition test in the Wistar rat was initially developed by ENNACEUR and DECACOUR (Behav. Brain Res., 1988, 31, 47–59). The test is based on the spontaneous exploratory activity of the animal and has the characteristics of episodic memory in humans. This memory test is sensitive to ageing (SCALL et al., Eur. J. Pharmacol., 1997, 325 173–180) and to cholinergic dysfunctions (BARTOLINI et al., Pharm. Biochem. Behav. 1996, 53(2), 277–283) and is based on the differences in the exploration of 2 objects of fairly similar shape—one familiar, the other new. Prior to the test, the animals are habituated to the environment (an enclosure without an object). In the course of a first session, the rats are placed (3 minutes) in the enclosure, in which there are 2 identical objects. The duration of exploration is measured for each object. In the course of the second session (3 minutes), 24 hours later, 1 of the 2 objects is replaced by a new object. The duration of exploration is measured for each object. The assessment criterion is the difference, Delta, expressed in seconds, between the exploration times for the new object and for the familiar object in the course of the second session. The control animals, previously treated with the carrier either by the IP route 30 minutes before each session, or by the oral route 60 minutes before each session, explore the familiar object and the new object in an identical manner, which indicates that the object introduced earlier has been forgotten. Animals treated with a compound that facilitates mnemocognition preferentially explore the new object, which indicates that the object introduced earlier has been remembered.

The results obtained show a difference, Delta, of from 5 to 10 s, for doses ranging from 0.3 to 3 mg/kg by the IP route and ranging from 3 to 30 mg/kg by the oral route, which shows that the compounds of the invention greatly enhance memorisation, even at a low dose.

EXAMPLE 11

Pharmaceutical composition

| Formulation for the preparation of 1000 tablets each containing 10 mg of active ingredient: | |
|---|---|
| Compound of Example 1 | 10 g |
| Hydroxypropylcellulose | 2 g |
| Wheat starch | 10 g |
| Lactose | 100 g |
| Magnesium stearate | 3 g |
| Talc | 3 g |

We claim:

1. A compound selected from those of formula (I):

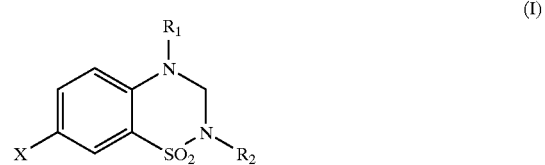

wherein:

X represents fluorine, bromine, iodine or methyl, each of $R_1$ and $R_2$, which may be identical or different, represents hydrogen or linear or branched ($C_1$–$C_6$) alkyl, its isomers when they exist, or addition salts thereof with a pharmaceutically acceptable acid.

2. A method of treating a living animal body afflicted with cognitive defects associated with cerebral aging and neurodegenerative pathologies, comprising the step of administering to the living animal body an amount of a compound of claim 1 which is effective for alleviation of said condition.

3. A pharmaceutical composition comprising as active principle an effective amount of a compound of claim 1, together with one or more pharmaceutically acceptable excipients or vehicles.

* * * * *